(12) United States Patent
Elberling et al.

(10) Patent No.: US 11,832,952 B2
(45) Date of Patent: Dec. 5, 2023

(54) SYSTEM AND METHOD FOR GENERATING AND RECORDING AUDITORY STEADY-STATE RESPONSES WITH A SPEECH-LIKE STIMULUS

(71) Applicant: Interacoustics A/S, Middelfart (DK)

(72) Inventors: Claus Elberling, Virum (DK); James Michael Harte, Middelfart (DK)

(73) Assignee: Interacoustics A/S, Middelfart (DK)

( * ) Notice: Subject to any disclaimer, the term of this patent is extended or adjusted under 35 U.S.C. 154(b) by 693 days.

(21) Appl. No.: 16/899,719

(22) Filed: Jun. 12, 2020

(65) Prior Publication Data

US 2020/0367783 A1    Nov. 26, 2020

Related U.S. Application Data

(62) Division of application No. 15/044,743, filed on Feb. 16, 2016, now Pat. No. 10,736,535.

(30) Foreign Application Priority Data

Feb. 16, 2015    (EP) ..................................... 15155203

(51) Int. Cl.
*A61B 5/12*      (2006.01)
*A61B 5/38*      (2021.01)
(Continued)

(52) U.S. Cl.
CPC ................ *A61B 5/38* (2021.01); *A61B 5/125* (2013.01); *A61B 5/6815* (2013.01); *H04R 25/70* (2013.01);
(Continued)

(58) Field of Classification Search
CPC ......... A61B 5/38; A61B 5/125; A61B 5/6815; H04R 2225/43
See application file for complete search history.

(56) References Cited

U.S. PATENT DOCUMENTS

| | | |
|---|---|---|
| 4,390,748 A | 6/1983 | Zwicker |
| 5,282,475 A | 2/1994 | Urbach et al. |

(Continued)

FOREIGN PATENT DOCUMENTS

| | | |
|---|---|---|
| EP | 2 581 038 A1 | 4/2013 |
| WO | WO 2006/003172 A1 | 1/2006 |

OTHER PUBLICATIONS

Bisgaard et al., "Standard Audiograms for the IEC 60118-15 Measurement Procedure", 2010, https://www.ncbi.nlm.nih.gov/pmc/articles/PMC4111352/.

(Continued)

*Primary Examiner* — Daniel L Cerioni
(74) *Attorney, Agent, or Firm* — Birch, Stewart, Kolasch & Birch, LLP

(57) ABSTRACT

A diagnostic system for recording auditory steady-state responses of a person comprises a) a stimulation unit for providing an acoustic stimulus signal to an ear of the person, and b) a recording unit for recording the auditory steady-state responses of the person origination from said acoustic stimulus signal, wherein the stimulation unit is configured to provide that the acoustic stimulus signal comprises a speech-like stimulus provided as a combination of a series of individual frequency-specific stimuli, each having a specified, e.g. predetermined, frequency bandwidth, presentation rate, amplitude and amplitude-modulation. The application further relates to a combined system comprising a diagnostic system and a hearing aid. The invention may e.g. be used for diagnostic instruments for verifying the fitting of a hearing aid.

11 Claims, 8 Drawing Sheets

(51) Int. Cl.
  *A61B 5/00*   (2006.01)
  *H04R 25/00*   (2006.01)
(52) U.S. Cl.
  CPC ...... *H04R 2225/43* (2013.01); *H04R 2430/03* (2013.01)

(56) References Cited

U.S. PATENT DOCUMENTS

| | | |
|---|---|---|
| 8,591,433 B2 | 11/2013 | Elberling |
| 2004/0064066 A1 | 4/2004 | John et al. |
| 2008/0033317 A1 | 2/2008 | Elberling |
| 2012/0197153 A1 | 8/2012 | Kraus et al. |
| 2014/0029777 A1 | 1/2014 | Jang |

OTHER PUBLICATIONS

Rønne et el., "Modeling auditory evoked brainstem responses to transient stimuli", The Journal of the Acoustical Society of America, American Institute of Physics for the Acoustical Society of America, vol. 131, No. 5, May 2012, pp. 3903-3913.

SYSTEM AND METHOD FOR GENERATING AND RECORDING AUDITORY STEADY-STATE RESPONSES WITH A SPEECH-LIKE STIMULUS

CROSS-REFERENCE TO RELATED APPLICATIONS

This application is a Divisional of co-pending application Ser. No. 15/044,743, filed on Feb. 16, 2016, which claims priority under 35 U.S.C. § 119(a) to application Ser. No. 15/155,203.1, filed in the European Patent Office on Feb. 16, 2015, all of which are hereby expressly incorporated by reference into the present application.

TECHNICAL FIELD

The present application relates to a method of recording Auditory Evoked Potentials (AEP), in particular Auditory Steady State Responses (ASSR). The disclosure relates specifically to a method of recording auditory evoked potentials of a person (a human being). The application also relates to a data processing system comprising a processor and program code means for causing the processor to perform at least some of the steps of the method.

The application furthermore relates to a system for recording auditory evoked potentials of a person, and to its use.

Embodiments of the disclosure may e.g. be useful in applications such as diagnostic instruments for verifying fitting of a hearing aid.

BACKGROUND

When transient sounds are presented to human subjects, the summed response from many remotely located neurons in the brain can be recorded via non-invasive electrodes (e.g. attached to the scalp and/or located in an ear canal of a person). These auditory evoked potentials (AEPs) can be recorded from all levels of the auditory pathway, e.g. from the auditory nerve (compound action potential, CAP); from the brainstem (auditory brainstem response, ABR); up to the cortex (cortical auditory evoked potential, CAEP), etc. These classical AEPs are obtained by presenting transient acoustic stimuli at slow repetition rates. At more rapid rates, the responses to each stimulus overlap with those evoked by the preceding stimulus to form a steady-state response (as defined in [Picton et al., 1987]). In early studies, such auditory steady-state responses (ASSR) were also evoked by sinusoidally amplitude modulated (AM) pure tones. Due to the tonotopic organisation of the inner ear (the cochlea) and auditory pathway, the carrier frequency for AM tones determines the region of the basilar membrane within the cochlea being excited, but producing evoked responses that follow the modulation frequency. In this way, ASSR has proved to be an efficient tool for testing different frequency locations within the auditory pathway. AM tones are the simplest frequency specific stimuli used to evoke ASSRs, but they only stimulate a small number of auditory nerve fibres resulting in relatively small response amplitude. This small response can be problematic for response resolution, so various methods have been developed to increase area of excitation in the cochlea to recruit more auditory nerve fibres, and to increase response amplitude and hence response detection and accuracy.

WO2006003172A1 (U.S. Pat. No. 8,591,433 B2) describes the design of frequency-specific electrical or acoustical stimuli for recording ASSR as a combination of a series of multiple spectral components (i.e. pure tones), designed to optimise response amplitudes. This was achieved by pre-compensating for the frequency-dependent delay introduced in the inner ear (cochlea) to achieve more synchronised auditory nerve firing across frequency. It is a basic characteristic of an auditory evoked response that the magnitude of the response depends on the number of auditory units/nerve fibres that are activated synchronously by the stimulus (as defined in [Eggermont, 1977]). By compensating for the inherent cochlea frequency-dependent delay, and specifically defining the magnitude and phase of each of the multiple spectral components, a repetitive frequency glide or chirp can be created. The repetition rate of this chirp-train is determined from the frequency spacing between the spectral components used in its generation, and the bandwidth is controlled by the number of components chosen. In this way, a very flexible and efficient stimulus for recording ASSR can be created (cf. e.g. [Elberling, 2005], [Elberling et al., 2007a], [Elberling et al., 2007b] and [Cebulla et al., 2007]).

One of the major advantages of ASSR is the ability to perform simultaneous multi-band recordings, i.e. to present multiple stimuli at different carrier frequencies to both ears—each with different repetition rates, and hence detection and observation of these potentials are typically made in the frequency domain. The stimulus and response structure in the frequency domain are well-defined and importantly predictable, thus ASSR lends itself well to automatic detection algorithms based on sets of harmonics of the modulation/repetition rates.

At present, ASSRs in the clinic and in research are stimulated using repeated trains of broad-band and narrow-band chirps, amplitude modulated tones, combined amplitude and frequency modulated tones, and trains of clicks and tone-bursts. As a result of highly successful universal newborn screening programs in many countries, paediatric audiologists are now routinely seeing patients within the first-few weeks of life (Chang et al., 2012). Therefore, it is advantageous to have hearing aid fitting protocols designed for young infants, as the sooner the intervention then the better the clinical outcomes. Thus the use of ASSR for estimating audiometric threshold is fast gaining ground for use with neonates referred from a screening programme. Determining these patients' thresholds via behavioural measures is highly unreliable or impossible, hence the need for objective physiological methods. Regression statistics exist to calculate the expected difference between physiologic and behavioural thresholds at each sound level. Accurate threshold estimation depends on being able to determine whether a small response exists in the presence of residual background noise. In addition to infants, ASSR and objective measures are used with hard to test adults, i.e. adults with severe mental or physical impairment.

Once a hearing aid is fitted to a particular user, then parameters need to be adjusted, for example to ensure that gain is set such that the speech spectrum is amplified within the dynamic hearing range of the subject. For good practice, a verification of this fitting needs to be made to ensure that this is in fact the case. A robust objective method for doing this is important. Sound field auditory evoked potentials—ABR, CAEP and ASSR have all been proposed as potential methods for doing this. It has been shown that ABRs are inappropriate, as the stimuli used to evoke them are typically very short (<10 ms), and hearing aid processing distorts the stimulus, making the response waveform hard to interpret.

CAEPs are growing in popularity for verification of hearing aid fitting. In particular, CAEPs evoked from short-duration phonemes and speech-like stimuli are argued to reflect neural encoding of speech and provide objective evidence that the amplified speech has been detected. CAEPs have documented disadvantages that they are strongly affected by the attention of the subject, which is hard to control in infants. Also, objective detection of response waveforms is challenging as the waveforms/evoked potentials vary significantly across subjects. Finally, even though they are longer in duration than ABR stimuli, typical stimuli to evoke CAEPs are still relatively short, and hence are subject to the same distortion and disadvantage as described above.

SUMMARY

The present disclosure relates to the field of recording Auditory Evoked Potentials (AEPs) from human participants. The present disclosure aims at reducing at least some of the disadvantages of prior art solutions. Specifically, the disclosure focuses on a new technique for stimulating Auditory Steady State Responses with a more speech-like signal, including amplitude variations over time that is similar to free-running speech.

This present disclosure is concerned with making ASSR stimuli, more speech-like, while still retaining their advantageous properties. This may be used in the verification of hearing aid fitting application described above, as it circumvents some of the challenges seen with cortical evoked responses. However, equally the method may be used to record an unaided response, with the advantage of exciting the auditory system with a signal capable of assessing its ability to process speech.

The present disclosure proposes to spectrally shape multi-band ASSR stimuli to have a normal long-term speech spectrum. Imposed on this will be a low-frequency amplitude modulation similar to the envelope seen in free-running speech (cf. e.g. [Plomp; 1984]). For sounds, which convey information, such as speech, much of the information is carried in the changes in the stimulus, rather than in the parts of the sound that are relatively stable. Normal multi-band ASSR with different separate carrier frequencies or bands will for each band have a different modulation or repetition rate. This allows multiple band detection of the response in the frequency domain. The different repetition rates and bands summed up in the time domain will result in a stimulus that has a waveform that will vary over time. The present disclosure proposes additionally to apply a low-frequency amplitude modulation in the range of the normal modulation spectrum of speech (cf. e.g. [Plomp; 1984] . . . <20 Hz), in order to make the stimulus more speech-like, i.e. to have realistic amplitude fluctuations similar to free-running speech.

How a hearing aid (HA) processes incoming auditory stimuli is extremely important if the desired application is using ASSR for verification of fitting. A HA is a medical device designed to amplify incoming sounds to make them audible for the wearers, and to improve their speech intelligibility. Modern digital HAs are complex nonlinear and non-stationary (time-varying) devices, that change their state or mode of operation based on an on-going estimation of the type and characteristics of the sound being presented to them. For instance, the amount of dynamic gain being applied may depend on whether the stimulus is speech, music, random noise or dynamic environmental sounds, objectively estimated in the signal processing algorithms of the HAs. In verification of fitting applications in infants and hard to test individuals (e.g. adults), we are predominantly interested in whether that individual's HAs are programmed such that speech at normal listening levels is amplified to be within the listener's audible range. It is important then, that any new ASSR stimulus is processed by the HA in a similar way to real free-running speech. The present disclosure proposes to modify the ASSR stimuli to be more speech-like, e.g. by introducing appropriate amplitude variations over time. Insertion gain measurements from different HAs can be made according to IEC 60118-15 (2012), to verify that the stimuli are being processed in a speech-like manner.

The exact neuro-physiological generator site is ambiguous with ASSR, as the whole auditory system responds when excited. Changing the repetition rates of the multi-band ASSR stimulus shifts the region of the auditory system that dominates the power of the response that is recorded at the surface of the scull. Auditory steady state responses at repetition rates <20/s are believed to be predominantly of cortical origin. For rates >20/s, the responses are generally believed to be generated by both cortical and brainstem sources, with the strength of the cortical activity decreasing with increasing repetition rate. Above approximately 50 Hz it is generally accepted that brainstem sources dominate. Special mention should be given to the rates close to 40/s, here the responses are generated both by the brainstem, the primary auditory cortex and thalamocortical circuits (cf. e.g. [Picton et al.; 2003] and [Kuwada et al.; 2002]). Responses higher in the auditory pathway than the brainstem are affected by attention and state of arousal. Also there is a significant maturational effect for cortical responses—with neonates' having small 40/s ASSR amplitudes, due to this. However rates in the range around 70/s to 100/s produce robust and solid responses, that are not overly affected by state of arousal and certainly not attention, maturational effects attributed to neural immaturity and developmental changes in the acoustics of the ear canal or middle ear. Therefore by varying modulation or repetition rate it is possible to shift the location of the ASSR generation mechanism to different locations in the auditory pathway (i.e. brainstem to cortex) depending on what is needed in the application in question.

The modification to the ASSR stimulus proposed here presents a new approach to obtain speech-like stimuli. In embodiments of the disclosure, information about the neural encoding of speech stimuli may be extracted, whilst retaining the excellent detection statistics in ASSR recording.

An object of the present application is to excite the auditory system with a signal capable of assessing the auditory systems ability to process speech. A further object of embodiments of the application is to create a stimulus for driving a hearing aid in a speech-like manner in order to objectively asses the hearing ability of a user while wearing the hearing aid.

Objects of the application are achieved by the invention described in the accompanying claims and as described in the following.

A Method for Recording Auditory Steady-State Responses of a Person:

In an aspect of the present application, an object of the application is achieved by a method for recording auditory steady-state responses of a person, the method comprising a) providing an acoustic stimulus signal to an ear of the person, b) recording the auditory steady-state responses of the person originating from said acoustic stimulus signal. The method provides that, the acoustic stimulus signal comprises a speech-like stimulus. Preferably, the method comprises that the speech-like stimulus is provided as a combination (e.g. a summation, or a weighted sum) of a series of frequency-specific stimuli, each having a specified (e.g. predetermined) frequency bandwidth, presentation rate, amplitude and amplitude-modulation.

An advantage of the disclosure is that it allows a clinical assessment of the effect of a hearing device in a normal mode of operation, i.e. when processing speech stimuli.

An aim of the present disclosure is to provide a new way of evoking an ASSR, using a speech-like stimulus, yet still retaining the advantages of traditional approaches where the stimulus and response structure in the frequency domain are well-defined and predictable. This is e.g. achieved by using automatic algorithms for detection or amplitude (power) estimation based on a set of harmonics of the modulation/repetition rates within the different frequency bands of the stimulus.

In an embodiment, the method comprises
a1) designing an electrical stimulus signal representing a speech-like signal;
a2) converting said electrical stimulus signal to said acoustic stimulus signal;
a3) applying said acoustic stimulus signal to an ear of the person.

Preferably, the application of the acoustic stimulus to an ear of the person is performed in a free-field configuration (from a loudspeaker, e.g. a directional loudspeaker, that is located outside the ear canal of the person). Alternatively, the acoustic stimulus may be applied to the ear drum of the person (only) by a loudspeaker of a hearing device worn at or in an ear of the user. In the latter case, the stimuli may be transmitted to or generated in the hearing device.

In an embodiment, the method comprises recording said auditory evoked responses of the person
    When the person is wearing a hearing device at the ear; as well as
    When the person is not wearing the hearing device at the ear.

It is anticipated that the person has a hearing impairment at one or both ears, and that the hearing device (e.g. a hearing aid) is configured for compensating for a hearing impairment of an ear of the person exhibiting such hearing impairment.

It is understood that the hearing device, when exposed to the acoustic stimulus, is turned on. In an embodiment, the person has a hearing impairment at one or both ears. Preferably, the hearing device (e.g. a hearing aid) is configured to compensate for a hearing impairment of that ear of the person.

In an embodiment, the speech-like stimulus is created as an electric stimulus signal, which is converted to an acoustic signal (e.g. by an electro-acoustic transducer, e.g. a vibrator or a loudspeaker). In an embodiment, the speech-like stimulus is created as an acoustic signal composed of a number of individual acoustic signal components that together (e.g. when mixed, e.g. added) represent the speech-like stimulus.

In an embodiment, the method comprises that the presentation rates of the individual frequency-specific stimuli are configurable. In an embodiment, the method comprises that the presentation rates of the individual frequency-specific stimuli are different and chosen to be appropriate for the recording of the auditory evoked responses in response to multiple, simultaneous, frequency-specific stimuli, and for obtaining responses from the appropriate structures of the auditory pathway. By choosing different modulation/repetition rates for different frequency bands (e.g. one-octave wide) it is possible to simultaneously test different frequency regions of the auditory system. The ASSR response spectrum to a single band comprises a series of harmonics at multiples of the modulation/repetition rate. Thus if multiple bands are presented simultaneously, but each band has its own unique modulation/repetition rate, then the physiological evoked response will contain multiple harmonic series, but importantly at distinct frequencies. This will allow separation of the responses from the different bands.

In an embodiment, the method comprises that a combined amplitude-spectrum of individual frequency-specific stimuli corresponds to a long-term amplitude spectrum of normal speech. In an embodiment, the combined amplitude-spectrum is a combination of a multitude of (e.g. three or more, such as four or more, or eight or more) individual frequency-specific stimuli. In an embodiment, each of the frequency-specific stimuli (for instance four one-octave wide Chirp stimuli, see e.g. [Elberling et al., 2007b]) is weighted such that the overall broad-band stimulus has a long-term spectrum which approximates that of normal speech.

In an embodiment, the method comprises that either a combined broad-band stimulus of the individual frequency-specific stimuli or the individual frequency-specific stimuli are amplitude-modulated corresponding to a corresponding low-frequency modulation which occurs in normal speech. In an embodiment, low-frequency amplitude modulation similar to that seen in free-running speech is applied to the broad-band speech spectrum shaped ASSR stimulus. The low frequency amplitude modulation and long-term speech spectrum will preferably ensure that hearing aids will process the combined stimulus in a way similar to free-running speech. In an embodiment, the term 'low-frequency modulation which occurs in normal speech' is e.g. taken to mean the resulting stimulus having a modulation spectrum comparable to normal speech, e.g. with a maximum around 4 Hz when measured in 1/3 octave bands (cf. e.g. [Plomp, 1984]).

In an embodiment, the method provides that the long-term amplitude-spectrum and the low frequency amplitude-modulation of the individual frequency-specific stimuli corresponds to speech spoken with a specific vocal effort. In an embodiment, examples of speech spoken with a specific vocal effort is represented by Soft, Normal, Raised, and Shouted. In an embodiment, a combined broad-band stimulus having a long-term averaged spectrum is provided at levels defined in terms of specific vocal effort according to ANSI S3.5. (1997). This is advantageous for clinical applications aimed at testing at standardised speech levels.

In an embodiment, the method provides that the individual frequency-specific stimuli consist of band-limited chirps. In an embodiment, the individual frequency-specific chirps are one-octave wide. In an embodiment, the individual frequency-specific chirps are configured to cover the frequency range from relevant for speech intelligibility, e.g. adapted to the specific person, e.g. covering a frequency in the range between 200 Hz and 8 kHz, e.g. a range between approximately 350 Hz to 5600 Hz. In an embodiment, the frequency-specific stimuli consist of four, one-octave wide chirps having the center frequencies 500, 1000, 2000 and 4000 Hz, respectively, thus covering the frequency range from approximately 350 Hz to 5600 Hz.

In an embodiment, the method provides that the recording of said auditory evoked responses comprises recording of auditory steady-state responses, ASSR.

A Method of Designing Stimuli:

In an aspect, a method of designing stimuli for an ASSR system is provided. The method comprises:

- Defining a number of different frequency specific stimuli, each having a specific frequency or center frequency and bandwidth;
- Defining an individual modulation rate or a repetition rate for each of the different frequency specific stimuli;
- Spectrally shaping the amplitude spectrum of each of the different frequency specific stimuli to provide spectrally shaped frequency specific stimuli;
- Combining the spectrally shaped frequency specific stimuli to provide a combined broad-band signal;
- Wherein the spectral shaping of the amplitude spectrum of each of the different frequency specific stimuli is configured to provide that the combined signal corresponds to the long-term spectrum of running speech spoken with a specific vocal effort;
- Amplitude modulating either each of the spectrally shaped frequency specific stimuli or the combined broad-band signal with a real or simulated envelope of running speech.

It is intended that some or all of the process features of the method of recording auditory evoked responses described above, in the 'detailed description of embodiments' or in the claims can be combined with embodiments of the method of designing stimuli for an ASSR system, when appropriate, and vice versa.

In an embodiment, the number of frequency specific stimuli is larger than or equal to two, such as larger than three, e.g. equal to four. In an embodiment, the number and the frequencies or center frequencies of the frequency specific stimuli are adapted to cover a predefined the frequency range, e.g. a range of operation of a particular hearing device or a frequency range of importance to speech intelligibility, e.g. part of the frequency range between 20 Hz and 8 kHz, e.g. between 250 Hz and 6 kHz.

A Stimulation System:

In an aspect, a stimulation system for designing and generating stimuli for an ASSR system is provided. The stimulation system comprises:

- A stimulation generator for generating a number of different frequency specific stimuli, each having a specific frequency or center frequency and bandwidth, and (the stimulation generator being) configured to apply an individual modulation rate or a repetition rate to each of the different frequency specific stimuli;
- A spectral shaping unit for spectrally shaping the amplitude spectrum of each of the different frequency specific stimuli to provide spectrally shaped frequency specific stimuli;
- A combination unit for combining the spectrally shaped frequency specific stimuli to provide a combined broad-band signal; and
- An amplitude modulation unit for amplitude modulating either each of the spectrally shaped frequency specific stimuli or the combined broad-band signal with a real or simulated envelope of running speech:

wherein the spectral shaping of the amplitude spectrum of each of the different frequency specific stimuli is configured to provide that the combined signal corresponds to the long-term spectrum of running speech spoken with a specific vocal effort.

It is intended that some or all of the process features of the method of designing stimuli for an ASSR system described above, in the 'detailed description of embodiments' or in the claims can be combined with embodiments of the system of designing stimuli for an ASSR system, when appropriate, and vice versa.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Diagnostic System:

In an aspect, a diagnostic system for recording auditory steady-state responses of a person, the system comprising a stimulation unit for providing an acoustic stimulus signal to an ear of the person, and a recording unit for recording the auditory steady-state responses of the person origination from said acoustic stimulus signal is furthermore provided by the present application. The stimulation unit is configured to provide that the acoustic stimulus signal comprises a speech-like stimulus. The speech-like stimulus is preferably provided as a combination of a series of frequency-specific stimuli, each having a specified (e.g. predetermined) frequency bandwidth, presentation rate, amplitude and amplitude-modulation.

It is intended that some or all of the process features of the method described above, in the 'detailed description of embodiments' or in the claims can be combined with embodiments of the diagnostic system, when appropriately substituted by a corresponding structural feature and vice versa. Embodiments of the diagnostic system have the same advantages as the corresponding methods.

In an embodiment, the stimulation unit comprises

- A stimulation generator for generating a number of different frequency specific stimuli, each having a specific frequency or center frequency and bandwidth, and configured to apply an individual modulation rate or a repetition rate to each of the different frequency specific stimuli;
- A spectral shaping unit for spectrally shaping the amplitude spectrum of each of the different frequency specific stimuli to provide spectrally shaped frequency specific stimuli;
- A combination unit for combining the spectrally shaped frequency specific stimuli to provide a combined broad-band signal; and
- An amplitude modulation unit for amplitude modulating either each of the spectrally shaped frequency specific stimuli or the combined broad-band signal with a real or simulated envelope of running speech to provide said speech-like stimulus, wherein the spectral shaping of the amplitude spectrum of each of the different frequency specific stimuli is configured to provide that the combined signal corresponds to the long-term spectrum of running speech spoken with a specific vocal effort.

In an embodiment, the combination unit comprises or is constituted by a SUM-unit for adding the individual spectrally shaped frequency specific (band-limited) stimuli to provide a combined broad-band signal. In an embodiment, the combination unit comprises or is constituted by a summation unit.

In an embodiment, the diagnostic system is configured to record auditory evoked responses (e.g. ASSR) of the person

- When the person is wearing a hearing device at the ear; as well as
- When the person is not wearing the hearing device at the ear.

A Combined System:

In an aspect, a combined system comprising a diagnostic system as described above, in the 'detailed description of embodiments' or in the claims and a hearing device for compensating a user's hearing impairment is furthermore provided.

In an embodiment, the hearing device is adapted to provide a frequency dependent gain and/or a level dependent compression and/or a transposition (with or without frequency compression) of one or frequency ranges to one or more other frequency ranges, e.g. to compensate for a hearing impairment of a user. In an embodiment, the hearing device comprises a signal processing unit for enhancing input signals and providing a processed output signal. Preferably, the hearing device is configured—at least in a specific mode of operation—to enhance speech intelligibility of a user.

Use:

In an aspect, use of a diagnostic system as described above, in the 'detailed description of embodiments' and in the claims, is moreover provided. In an embodiment, use of a diagnostic system to verify a fitting of a hearing aid is provided. In an embodiment, use of a diagnostic system to record ASSR on a person wearing a hearing aid (configured to compensate for the person's hearing impairment) is provided (aided measurement). In an embodiment, use of a diagnostic system to record ASSR on a person not wearing a hearing aid is provided (unaided measurement).

A Hearing Device:

In an aspect, a hearing device is furthermore provided. The hearing device comprises an input unit and an output transducer. The hearing device is configured to receive or generate different frequency specific stimuli generated as defined by the method of designing stimuli for an ASSR system as descried above in the 'detailed description of embodiments' or in the claims. The hearing device is furthermore configured to present the different frequency specific stimuli as an acoustic stimulus via said output transducer of the hearing device.

In an embodiment, the hearing device comprises hearing aid.

In an embodiment, the input unit of the hearing device comprises one or more microphones for picking up sound from the environment, including e.g. acoustic stimulus from a loudspeaker of a diagnostic system according to the present disclosure. In an embodiment, the hearing device is configured to receive the different frequency specific stimuli from the diagnostic system via a wireless link. In an embodiment, the hearing device comprises a combination unit allowing the different frequency specific stimuli to be presented to the user via the output transducer (e.g. a loudspeaker), alone or in combination with electric sound signals picked up or received by the input unit.

Definitions

The term 'a speech-like signal' or 'speech-like stimuli' is in the present context taken to mean a signal (or stimuli) that has a long-term spectrum and amplitude variations over time that are similar to free-running speech (as e.g. defined by IEC 60118-15. (2012)). Preferably, the speech like signal (or stimuli) is configured to exhibit level fluctuations (low frequency amplitude modulation) with a dynamic range over time in the free-field corresponding to speech, as e.g. defined in the IEC60118-15 standard (e.g. when analysed in 1/3-octave bands).

In the present context, a 'hearing device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing device may comprise a single unit or several units communicating electronically with each other.

More generally, a hearing device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing devices, an amplifier may constitute the signal processing circuit. In some hearing devices, the output means may comprise an output transducer, such as e.g. a loudspeaker for providing an air-borne acoustic signal or a vibrator for providing a structure-borne or liquid-borne acoustic signal. In some hearing devices, the output means may comprise one or more output electrodes for providing electric signals.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Figure 1A:
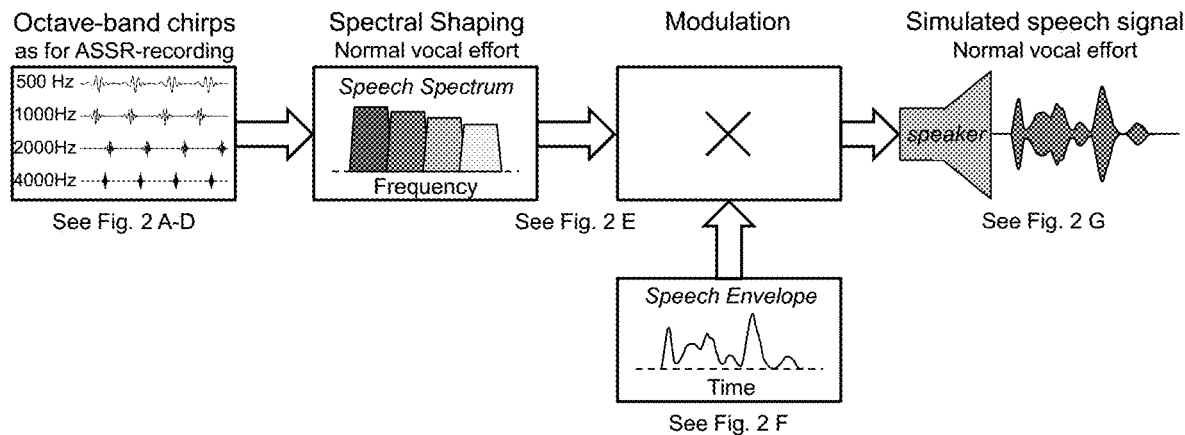
FIG. 1A schematically shows an embodiment of a method of generating a speech-like stimulus signal.
Figure 1B:
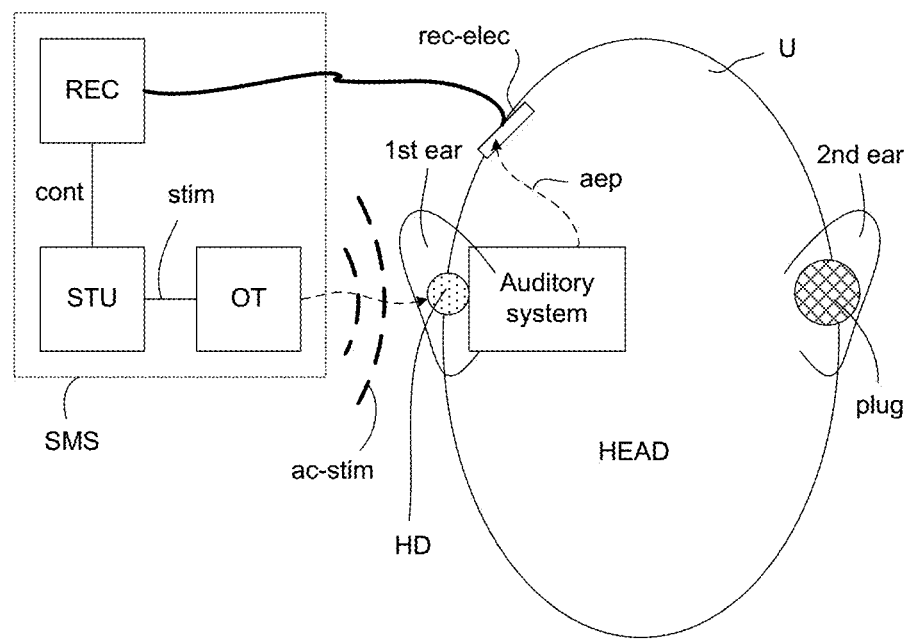
FIG. 1B shows an embodiment of diagnostic system for recording an auditory evoked potential according to the present disclosure.

FIG. 1A shows an embodiment of a method of generating a speech-like stimulus signal. FIG. 1B shows an embodiment of diagnostic system for recording an auditory evoked potential according to the present disclosure.

FIG. 1A shows the principle and preferred embodiment of the stimulus generation of the present disclosure. To the left (block Octave-band chirps), as an example, four octave-band Chirps are generated with the centre frequencies 500, 1000, 2000, and 4000 Hz. The stimuli are presented at different rates of stimulation (see e.g. FIG. 2A, 2B, 2C, 2D) and can be used for the simultaneous multiple frequency-specific stimulation of the ASSR (cf. e.g. WO2006003172A1, [Elberling et al., 2007b]). The four Chirps are next (cf. block Spectral Shaping) spectrally shaped so the amplitude spectrum of the combined signal corresponds to the long-term spectrum of running speech spoken with a specific vocal effort (here as an example the vocal effort is 'Normal'-ANSI S3.5. (1997)).

Next (cf. blocks Modulation), the combined and spectrally shaped signal is fed into an amplitude modulator, which modulates either each of the band-limited stimuli or the combined broad-band signal with a real or simulated envelope of running speech (cf. e.g. [Plomp, 1984]). Finally (cf. stage Simulated speech signal) the simulated speech signal is fed to a stimulus transducer (here a loudspeaker is shown as an example) with a presentation level as required.

In FIG. 1A references are made to the detailed temporal waveforms in FIG. 2A-2G.

FIG. 1A schematically illustrates an embodiment of a stimulation part (represented by STU and OT in FIG. 1B) of a diagnostic system. FIG. 1B schematically shows an embodiment of a diagnostic system (DMS) comprising a stimulation unit (STU), an output transducer (OT), and a recording unit (REC) in communication with a number of recording electrodes (rec-el). FIG. 1B further includes a user (U) wearing a hearing device (HD) at a $1^{st}$ ear ($1^{st}$ ear) and an ear plug (plug) at the $2^{nd}$ ear ($2^{nd}$ ear). FIG. 1B illustrates 'free field', aided measurement with a diagnostic system according to the present disclosure. The hearing device is adapted for picking up sound from the environment to provide an electric input signal, and comprises a signal processing unit for providing an improved signal by applying a level and frequency dependent gain to the input signal to compensate for a hearing impairment of the user's $1^{st}$ ear, and an output unit for presenting the improved signal as output stimuli perceivable by the user as sound. The ear plug (plug) is adapted to block sound at the $2^{nd}$ ear from evoking neurons in the auditory system. When electric stimuli (stim) generated by the stimulation unit (STU) and converted to acoustic stimuli (ac-stim) via output transducer (OT), the acoustic stimuli (ac-stim) are picked up by the input transducer of the hearing device(HD) at the first ear ($1^{st}$ ear) of the user (U), processed by the signal processing unit, and presented to the auditory system (Auditory system) of the user via the output unit of the hearing device. The stimuli from the output unit of the hearing device evokes responses (aep) from the auditory system (Auditory system). The evoked responses (aep) are recorded by the recording unit (REC) via recording electrodes (rec-el) mounted on the user's head (HEAD), e.g. attached to the skin and/or tissue of the user's scalp or ear canal. The recording (REC) and stimulation (STU) units are in communication (cf. signal cont), e.g. to control timing relations between the generation of stimuli by the stimulation unit and the detection and processing of evoked responses (ASSRs) by the recording unit.

FIG. 2A, 2B, 2C, 2D, 2E, 2F shows exemplary individual signal components from which a resulting speech-like stimulus signal (as illustrated in FIG. 2G) is generated.

FIG. 2A-2G shows the details of the time signals at the different stages of the proposed invention. From top to bottom: First the four frequency-specific stimuli are shown using a time scale of 100 ms (FIG. 2A-2D). The different rates of stimulation are indicated to the left and as an example vary from 84.0/s to 90.6/s. FIG. 2A shows a 500 Hz narrow band chirp with a stimulation rate (repetition rate) of 86.0 Hz. FIG. 2B shows a 1000 Hz narrow band chirp with a stimulation rate of 90.6 Hz. FIG. 2C shows a 2000 Hz narrow band chirp with a stimulation rate of 84.0 Hz. FIG. 2D shows a 4000 Hz narrow band chirp with a stimulation rate of 88.6 Hz. Each of the narrow band chirps is generated by respective filtering (with a 1 octave bandpass filter) of a broadband linear chirp between a minimum frequency (e.g. 350 Hz) and a maximum frequency (e.g. 11.3 kHz) (cf. [Elberling & Don, 2010]). The spectrally shaped combined broad-band signal is shown in FIG. 2E as the 'SUM of weighted Chirp signals'. In FIG. 2A-2G, four frequency-specific stimuli, each comprising a periodically repeated (1 octave wide) narrow band chirp, are used to generate the combined broad-band signal. Alternatively, another number of narrow band chirps may be used, e.g. 12 (1/3 octave wide) narrow band chirps covering the same frequency range from appr. 350 Hz to appr. 5600 Hz.

Next, using a time scale of 10 s, an example of a 'Simulated Speech Envelope' is shown in FIG. 2F, and finally the corresponding modulated output signal is shown as the 'Simulated Speech Signal' in FIG. 2G. The simulated speech envelope in FIG. 2E is e.g. generated as an envelope of exemplary free-running speech.

Figure 3:
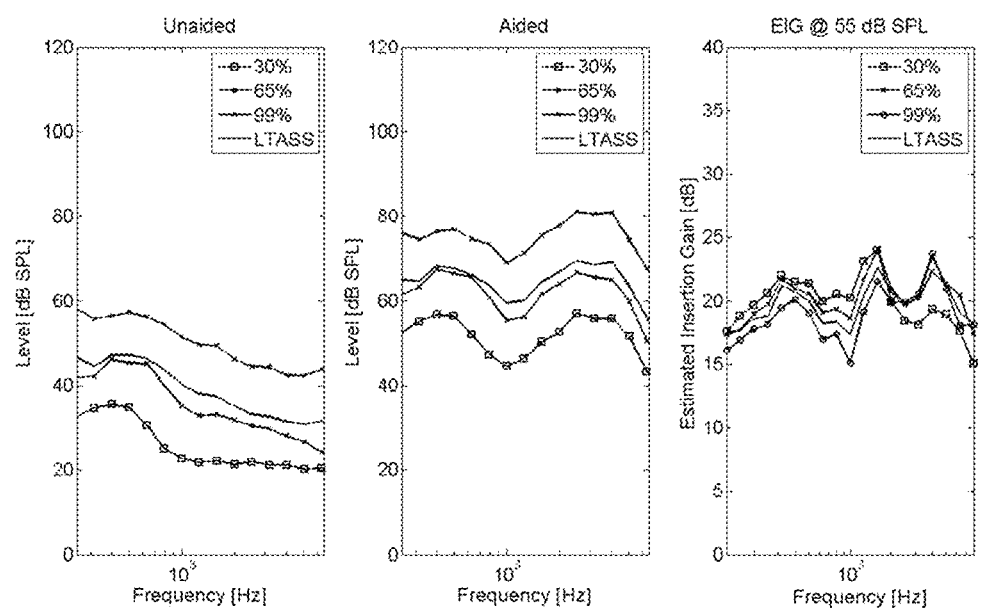
FIG. 3 shows an example of the IEC60118-15, (2012) method for determining hearing aid insertion gain and appropriate level dynamic range for speech-like stimuli.

FIG. 3 shows an example of the IEC60118-15, (2012) method for determining hearing aid insertion gain and appropriate level dynamic range for speech-like stimuli.

FIG. 3 gives an example of the IEC60118-15, (2012) method for determining hearing aid insertion gain and appropriate level dynamic range ([dB SPL] versus frequency [Hz]) for speech-like stimuli. On the left figure (denoted Unaided) is shown the level variations of a standardized speech test-stimulus ([Holube et al., 2010]) recorded in a hearing aid test-box (Interacoustics TB25). The level variation for each 1/3-octave band is indicated by the 30, 65 and $99^{th}$ percentiles of the corresponding distribution of the short-term (125 ms) amplitude values. Also shown is the long term amplitude speech spectrum (LTASS) in one-third octave bands. The middle figure (denoted Aided) shows the output from a paediatric hearing aid, measured in the test-box using an occluded-ear simulator (IEC 60318-4, 2010). On the right figure (denoted EIG=Aided-unaided@65 dB SPL) is shown the estimated insertion gain (EIG). It is observed that the estimated insertion gain of signal components having relatively lower input levels (represented by the 30% percentile) is larger than the estimated insertion gain of signal components having relatively higher input levels (represented by the 99% percentile). This is e.g. due to a compression algorithms, which tend to amplify low input levels more than high input levels. A preferred embodiment of the present invention is to use the methods set down in the IEC 60118-15, (2012)-standard to demonstrate the speech-like processing of the new ASSR stimuli with digital hearing aids.

Figure 4A:
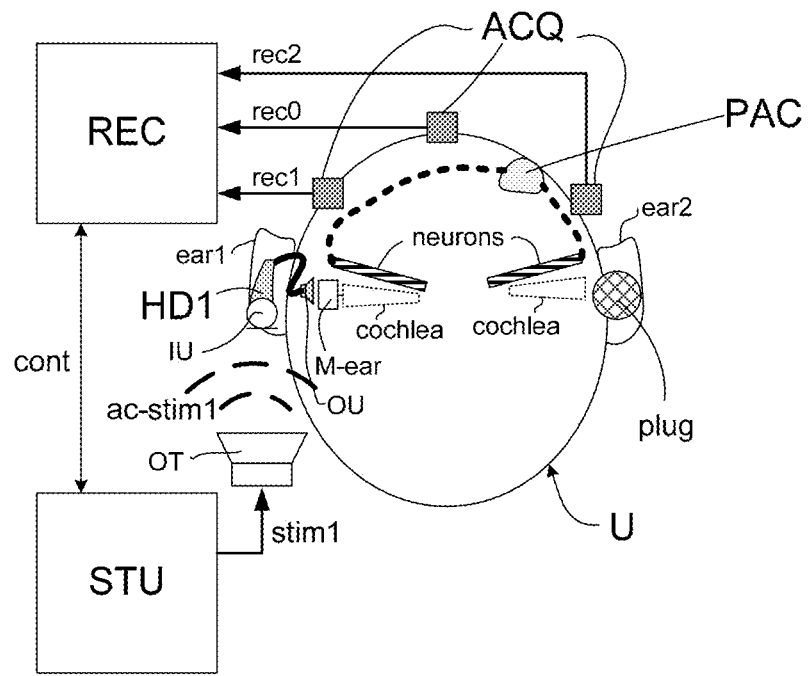
FIGS. 4A and 4B shows two exemplary setups of a diagnostic system for (together) verifying a fitting of a hearing aid, FIG. 4A illustrating an AEP measurement, where the user wears a hearing device in a normal mode (aided), and 4B illustrating an AEP measurement, where the user does not wear a hearing device (unaided), stimulation being in both setups provided via a loudspeaker of the diagnostic system.
Figure 4B:
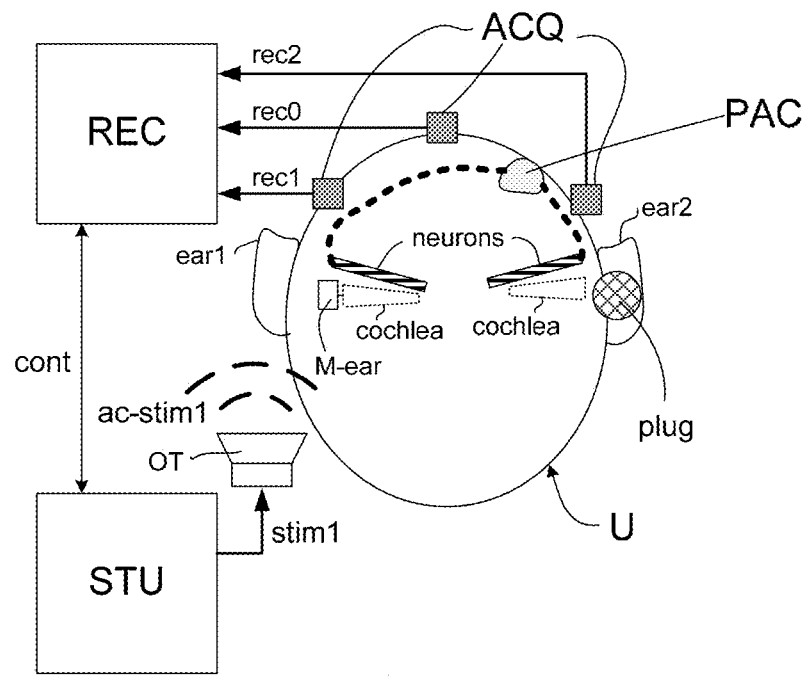

FIGS. 4A and 4B shows exemplary setups of a diagnostic system for verifying a fitting of a hearing aid, FIGS. 4A and 4B illustrating an AEP measurement, where the user wears a hearing device in a normal mode (aided), and where the user does not wear a hearing device (unaided), respectively. The diagnostic system comprises the components discussed in connection with FIG. 1B and is in FIG. 4A used in an aided measurement where free field acoustic stimuli (ac-stim1) from the output transducer (OT, here a loudspeaker) are picked up by a hearing device (HD1) adapted for being located in or at a first ear (ear1) of a user (U) (or fully or partially implanted in the head of the user). The hearing device comprises an input unit (IU, here a microphone is shown), a signal processing unit (not shown) for applying a level and frequency dependent gain to an input signal from the input unit and presented such enhanced signal to an output unit (OU, here an output transducer (loudspeaker) is shown). The output transducer of the hearing device is in general configured to present a stimulus (based on the signal picked up by the input unit IU), which is perceived by the user as sound. The auditory system of the user is schematically represented in FIGS. 4A and 4B by the ear drum and middle ear (M-ear), cochlea (cochlea) and the cochlear nerve (neurons). The nerve connections from the respective cochlear nerves to the auditory centre of the brain (the Primary Auditory Cortex, denoted PAC in FIGS. 4A and 4B) are indicated by the bold dashed curves in FIGS. 4A and 4B. The diagnostic system comprises a stimulation unit (STU) adapted to provide an electric stimulus signal (stim1) comprising a number of individually repeated frequency specific stimuli, which are combined and spectrally shaped in amplitude to emulate a long-term spectrum of running speech (at a certain vocal effort), and amplitude modulated in time to provide an envelope of the stimuli equivalent to that of running speech. The diagnostic system further comprises a recording unit (REC) for recording the auditory evoked responses of the person originating from said acoustic stimulus signal ac-stim1. In the scenario of FIG. 4B the free field acoustic stimulus signal ac-stim1 is received by the persons' ear and auditory system (without hearing aid means, i.e. in an 'unaided' mode). In the scenario of FIG. 4A the free field acoustic stimulus signal ac-stim1 is picked up, processed and presented to the person's auditory system by the hearing device (i.e. an 'aided' mode). In both the aided and unaided setup, the stimulation is provided at one ear (the right ear, ear1) and the other ear (the left ear, ear2) is provided with an ear plug (plug) to block sound that ear from evoking neurons in the auditory system. The recording unit comprises or is operationally connected to electrodes (ACQ) adapted to pick up brainwave signals (rec0, rec1, rec2) (e.g. AEPs) when appropriately located on the head of the user. In the embodiments of FIGS. 4A and 4B, three electrodes (ACQ) are shown located on the scalp of the user (U). The recording unit and the stimulation unit are in communication with each other (signal cont), e.g. to control a timing between stimulation and recording. The recording unit comprises appropriate amplification, processing, and detection circuitry allowing specific ASSR data to be provided.

Figure 5A:
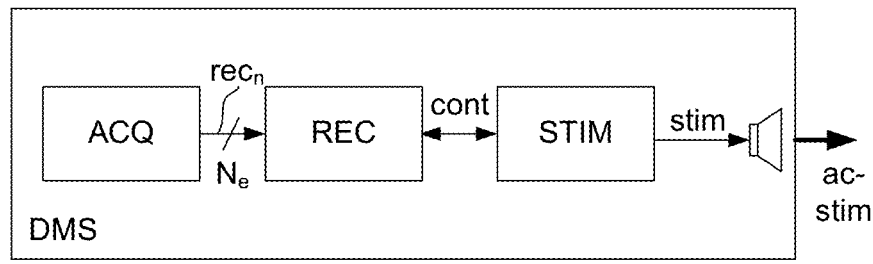
FIG. 5A shows an embodiment of a diagnostic system.
Figure 5B:
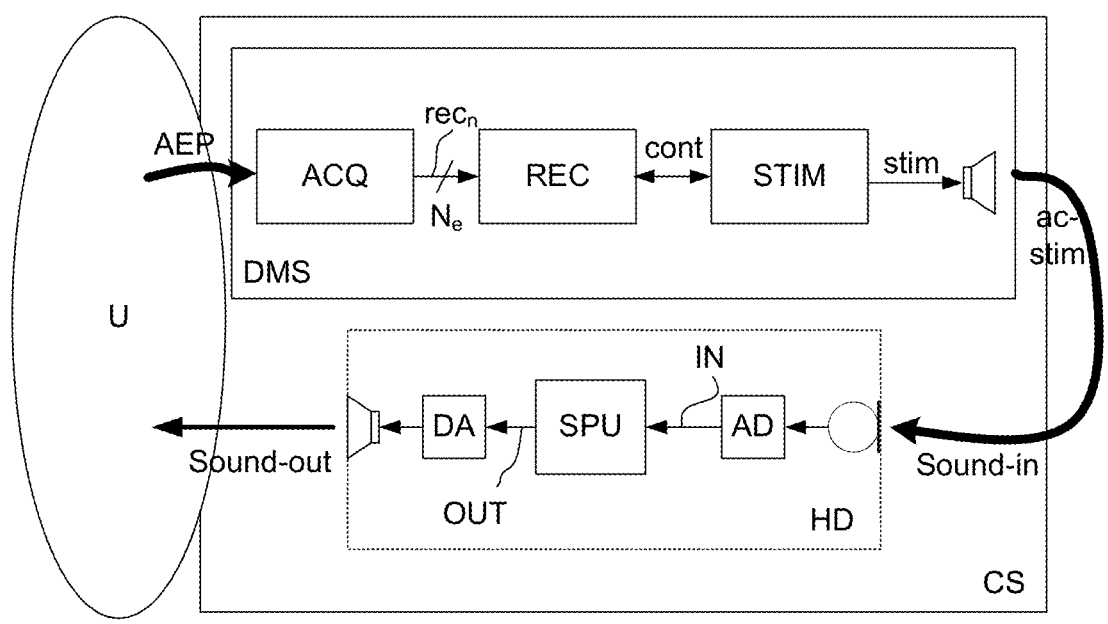
FIG. 5B shows an embodiment of a diagnostic system stimulating a hearing device while worn by a person, stimulation being provided via a loudspeaker of the diagnostic system.

FIG. 5A shows an embodiment of a diagnostic system alone, and FIG. 5B shows an embodiment of a diagnostic system stimulating a hearing device while worn by a person.

FIG. 5A is a block diagram of a diagnostic system (DMS) as also illustrated and described in connection with FIGS. 4A and 4B and in FIG. 1B. The diagnostic system comprises an electrode part (ACQ) comprising a number $N_e$ of electrodes for picking up evoked potentials $rec_n$ from the auditory system and brain when mounted on the head of the user. The evoked potentials $rec_n$ picked up by the electrodes are fed to the recording unit (REC) for processing and evaluation. Electric stimuli stim (e.g. controlled (e.g. initiated) by the recording unit (REC) via control signal cont) according to the present disclosure are generated by the stimulation unit (STIM) and converted to (free field) acoustic stimuli ac-stim by an output transducer (loudspeaker) of the system. FIG. 5B shows the diagnostic system (DMS) used in an 'aided' mode (as illustrated and discussed in connection with FIG. 4A), where a person wearing a hearing device (HD) is exposed to the acoustic stimuli (ac-stim) of the diagnostic system at one ear. The acoustic stimuli (ac-stim) are picked up by a sound input (Sound-in) of the hearing device located at the ear. The acoustic stimuli (ac-stim) are converted to an electric input signal by a microphone of the hearing device and processed in a forward signal path of the hearing device to a loudspeaker presenting the processed stimuli the user as an output sound (Sound-out). The forward path of the hearing device (HD) comprises e.g. an analogue to digital converter (AD) providing a digitized electric input signal (IN), a signal processing unit (SPU) for processing the digitized electric input, e.g. in a speech processing mode of operation, and providing a processed signal (OUT), which is converted to an analogue signal by a digital to analogue converter (DA) before it is converted to sound signal by the loudspeaker of the hearing device. The output sound (Sound-out) from the hearing device represents a processed version of the speech-like acoustic stimuli (ac-stim) from the diagnostic system (as delivered by the hearing device). The user's auditory system picks up the output sound (Sound-out) from the hearing device (HD) and evokes potentials (AEP) that are picked up by the electrodes (ACQ) of the diagnostic system (DMS). The diagnostic system (DMS) and the hearing device (HD) together represent a combined system (CS). The hearing device (HD) can be of any kind (type (air conduction, bone conduction, cochlear implant (or combinations thereof), style (behind the ear, in the ear, etc.) or manufacture) capable of enhancing a speech (or speech-like) input signal according to a user's needs. In an embodiment, the capability of the hearing device to process speech-like stimuli signals from the diagnostic system as ordinary speech is verified in a separate measurement (e.g. in a low-reflection measurement box), e.g. according to the IEC 60118-15 (2012)-standard, cf. further below.

EXAMPLE

Figure 2:
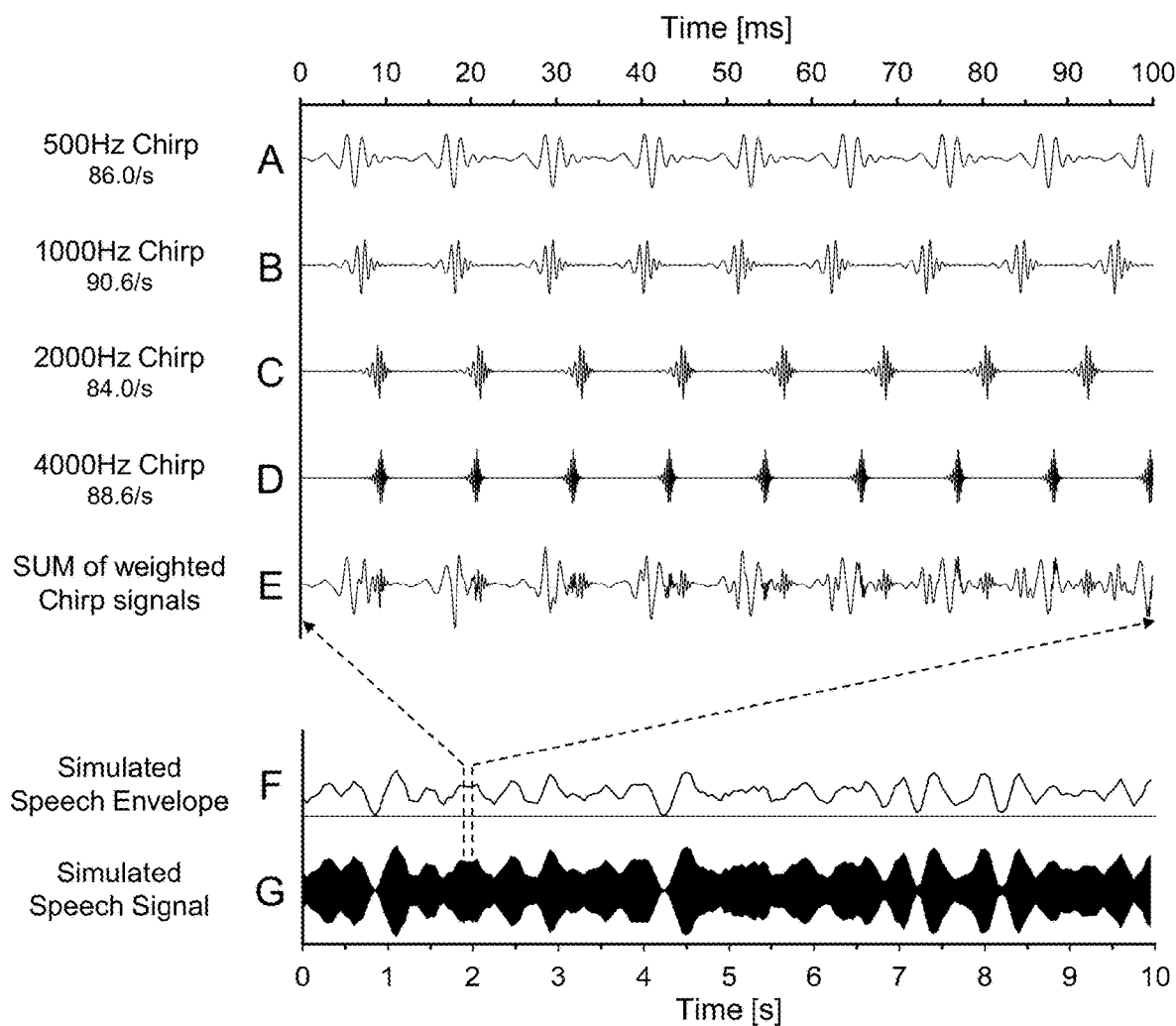
FIG. 2 shows exemplary individual signal components (A-F) from which a resulting speech-like stimulus signal (G) according to the present disclosure is generated.

As an example, the ASSR stimulus according to the present disclosure may be generated by four one-octave wide narrow-band (NB) chirp-train ASSR stimuli—constructed according to the methods described in U.S. Pat. No. 8,591,433 B2, and with centre frequencies 500, 1000, 2000, and 4000 Hz and repetition rates 86.0/s, 90.6/s, 84.0/s, and 88.6/s respectively. These examples are illustrated in FIG. 2 (A-D). To make the stimulus speech-like, the target sound pressure level should preferably correspond to normal speech levels in the octave bands. The stimulus should preferably be presented in a room with only minor reflections (e.g. anechoic). Each band is then weighted according to ANSI S3.5. (1997) for normal vocal effort speech measured at a distance of 1 m from the source (e.g. a loudspeaker). According to the ANSI-standard the octave-band sound pressure levels are then set to 59.8, 53.5, 48.8 and 43.9 dB SPL for the 500, 1000, 2000 and 4000 Hz octave bands respectively. The bands are then combined (see FIG. 2E), such that the sum of the individual bands will result in a broad-band stimulus with a long-term spectrum identical to speech at normal vocal effort, corresponding to a free-field sound pressure level of approximately 62.5 dB SPL.

Next the broad-band stimulus is fed to a modulator and the simulated speech envelope is applied. This is illustrated in FIG. 2F as a low-pass (4 Hz cut-off) filtered envelope of Gaussian white noise. The modulator multiplies the broad-band ASSR stimulus with the simulated speech envelope and the result is shown in FIG. 2G.

When presented through a hearing aid, the co-modulation of envelope power across bands and the fluctuation in band power will in principle excite the device in a mode of operation similar to speech. By using the IEC 60118-15 (2012)-standard, the appropriate acoustic measurements in a hearing aid analyser can be made to demonstrate that the stimulus is processed by the hearing aid in a manner similar to speech. Normal speech has inherent level fluctuations (amplitude modulation), the dynamic range of these over time in the free-field is an important characteristic for speech, and are analysed in 1/3-octave bands in the IEC60118-15 standard. If the new ASSR stimulus has the same input dynamic range as a standardised speech stimulus it is ensured that the hearing aid is stimulated correctly. The output from the hearing aid and the estimated insertion gain are also made to quantify this relationship and further demonstrate that the hearing aid is processing the stimulus in a speech-like manner. An example of this procedure is given in FIG. 3.

In the present example the AM is applied to the combined broad-band stimulus (cf. FIG. 2A-2G). Alternatively, the AM can be applied in a way as to simulate the co-modulation in normal speech, i.e. have narrow band regions with common modulation rather than across the full region of the broad-band stimulus. This could simply be done using a filter-bank and multiple-modulators before combining into a single broad-band stimulus. This is illustrated in FIG. 6.

Figure 6:
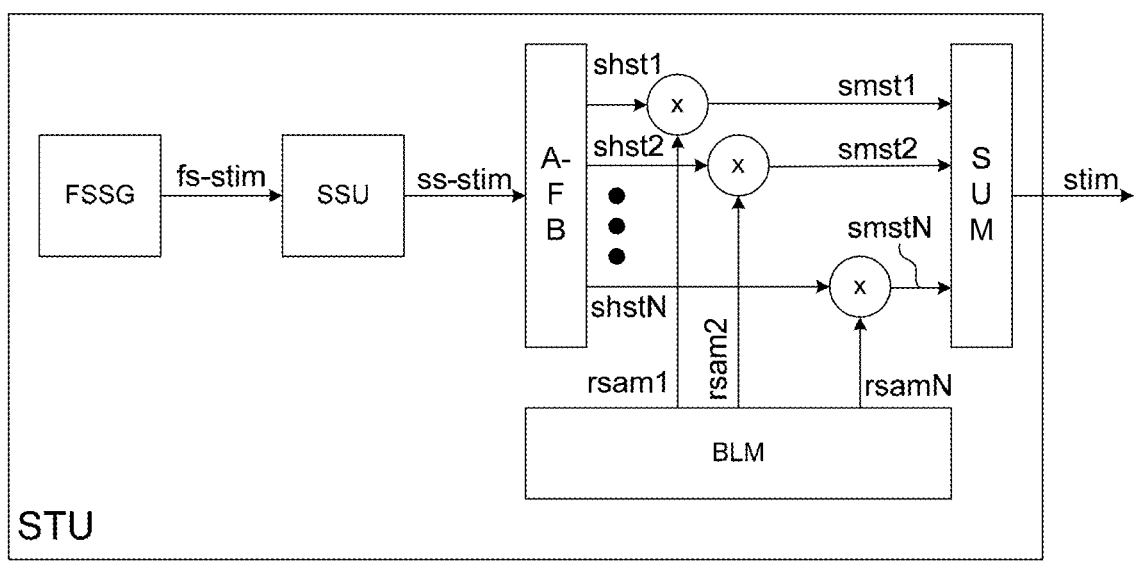
FIG. 6 shows an embodiment of a stimulation unit according to the present disclosure.

FIG. 6 shows an embodiment of a stimulation unit (STU) according to the present disclosure. The stimulation unit (STU) of FIG. 6 comprises a generator of frequency specific stimuli (FSSG), e.g. narrowband stimuli as shown in FIG. 1A, 1B, 2A-2G, but alternatively other frequency specific stimuli, e.g. stimuli generated by individual pure tones each tone amplitude modulated by a lower frequency carrier. The frequency specific stimuli generator (FSSG) provides stimuli signals fs-stim. The stimulation unit (STU) further comprises a spectrum shaping unit (SSU) that shapes the frequency specific stimuli fs-stim to provide that the amplitude spectrum of the resulting combined signal ss-stim corresponds to the long-term spectrum of running speech, e.g. spoken with a specific vocal effort. The stimulation unit (STU) further comprises an analysis filter-bank (A-FB) that splits the frequency shaped stimuli ss-stim in a number N of frequency bands, providing (time-varying) frequency shaped band signals shst1, shst2, . . . , shstN. The stimulation unit (STU) further comprises band-level modulators (denoted 'x' in FIG. 6) for amplitude modulating frequency shaped band signals shst1, shst2, . . . , shstN with individual band level modulation functions rsam1, rsam2, . . . , rsamN, provided by a band level modulation unit (BLM) configured to provide that the resulting amplitude modulated frequency shaped band signals smst1, smst2, . . . , smstN have an envelope equivalent to that of running speech. The stimulation unit (STU) further comprises a combination unit (here in the form of a SUM unit) to combine band level signals smst1, smst2, . . . , smstN to provide a resulting time-domain stimulation signal stim. The resulting electric stimuli stim may then be converted to acoustic stimuli (cf. ac-stim in FIGS. 1B, 4 and 5) by an electro-acoustic transducer (cf. e.g. OT in FIG. 1B), e.g. a loudspeaker (cf. e.g. speaker in FIG. 1A, 4, 5).

Figure 7A:
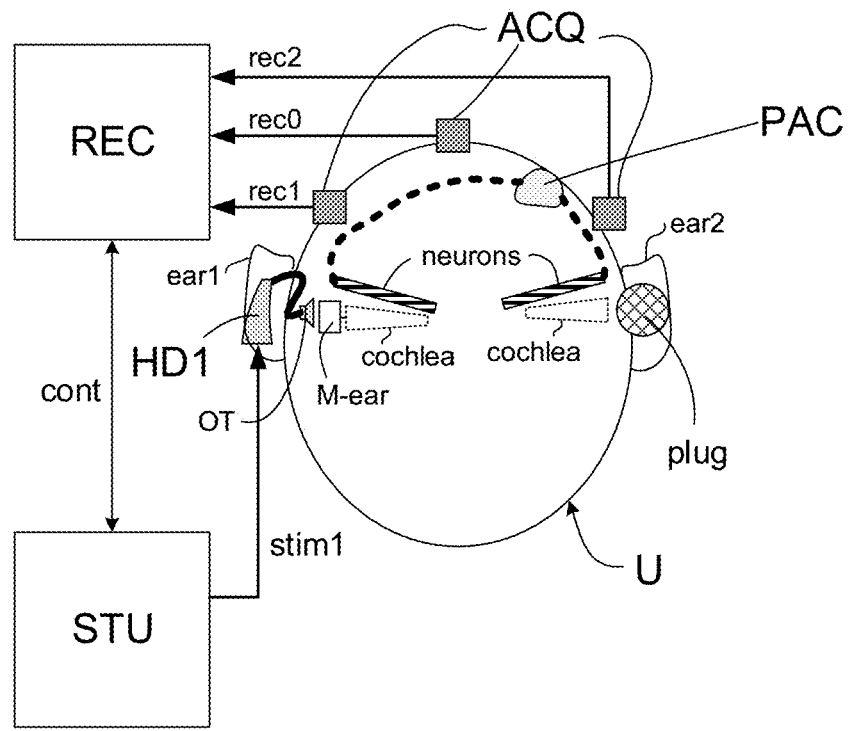
FIG. 7A shows a first scenario of an AEP measurement, where the user wears a hearing device in a normal mode (aided), and where stimuli are provided to the hearing device for being played to the user by a loudspeaker of the hearing device.
Figure 7B:
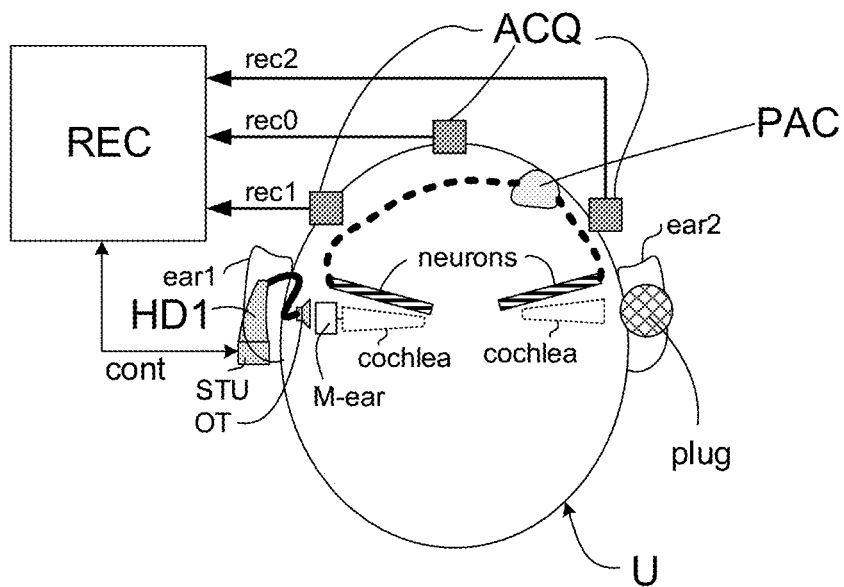
FIG. 7B shows a second scenario of an AEP measurement, where the user wears a hearing device in a normal mode (aided), and where stimuli are provided to the hearing device for being played to the user by a loudspeaker of the hearing device.
Figure 7C:
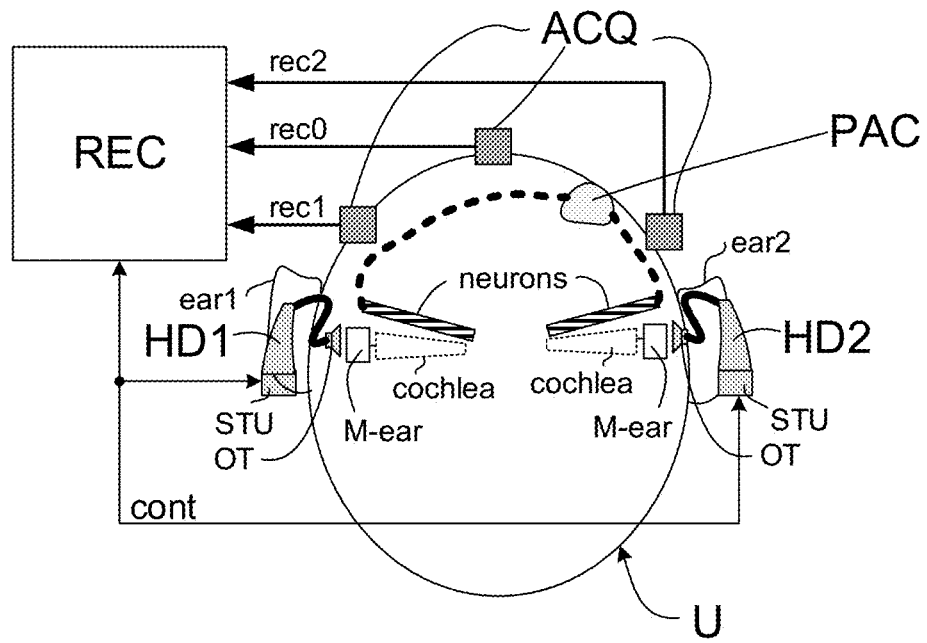
FIG. 7C shows a third scenario of an AEP measurement, where the user wears first and second hearing devices of a binaural hearing system in a normal mode (aided), and where stimuli are provided to the hearing devices for being played to left and right ears of the user by a loudspeaker of the hearing device.

FIGS. 7A, 7B, and 7C shows scenarios similar to those of FIG. 4A described above. A difference, though, is that the stimuli generated by the stimulation unit (STU) of the diagnostic system in the embodiments of FIG. 4A are transmitted (wired or wirelessly) directly to the hearing device(s) or are generated in the hearing device(s) (instead of being played via a loudspeaker of the diagnostic system and picked up by the microphone(s) of the hearing device(s)). In both cases, the stimuli are presented to the user (U via a loudspeaker (OT) of the hearing device (HD1).

FIG. 7A shows a first scenario of an AEP measurement, where the user (U wears a hearing device (HD1) in a normal mode (aided), and where stimuli stim1 are provided by a stimulation unit (STU) of the diagnostic system directly to the hearing device (HD1) for being played to the (U user by a loudspeaker (OT) of the hearing device (HD1). The connection between the diagnostic system and the hearing device may be a wired connection of a wireless connection (e.g. based on Bluetooth or other standardized or proprietary technology).

FIG. 7B shows a second scenario of an AEP measurement, where the user (U) wears a hearing device (HD1) in a normal mode (aided), and where stimuli stim1 are provided directly (electrically) to the hearing device for being played to the user by a loudspeaker of the hearing device. The embodiment of FIG. 7B is similar to the embodiment of FIG. 7A. A difference is though that the stimuli generated by the stimulation unit (STU) of the diagnostic system in FIG. 7A are generated in the hearing device (HD1) instead. The stimulation unit (STU) is located in the hearing device (HD1) and controlled by the diagnostic system via control signal cont (here) from the recording unit (REC) of the diagnostic system.

FIG. 7C shows a third scenario of an AEP measurement. The embodiment of FIG. 7C is similar to the embodiment of FIG. 7B. A difference is that in the embodiment of FIG. 7C, the user wears first and second hearing devices (HD1, HD2) of a binaural hearing system in a normal mode (aided) (instead of a single hearing device at one of the ears). Both hearing devices (HD1, HD2) comprise a stimulation unit (STU), which is controlled by the diagnostic system via control signal cont (here) from the recording unit (REC) of the diagnostic system.

An advantage of the embodiments of FIGS. 7A, 7B and 7C compared to the embodiment of FIG. 4A is that the stimuli are provided electrically to the loudspeaker of the hearing device (not via intermediate electric to acoustic transducer (loudspeaker of diagnostic system) and acoustic to electric transducer (microphone of hearing device)).

Figure 8:
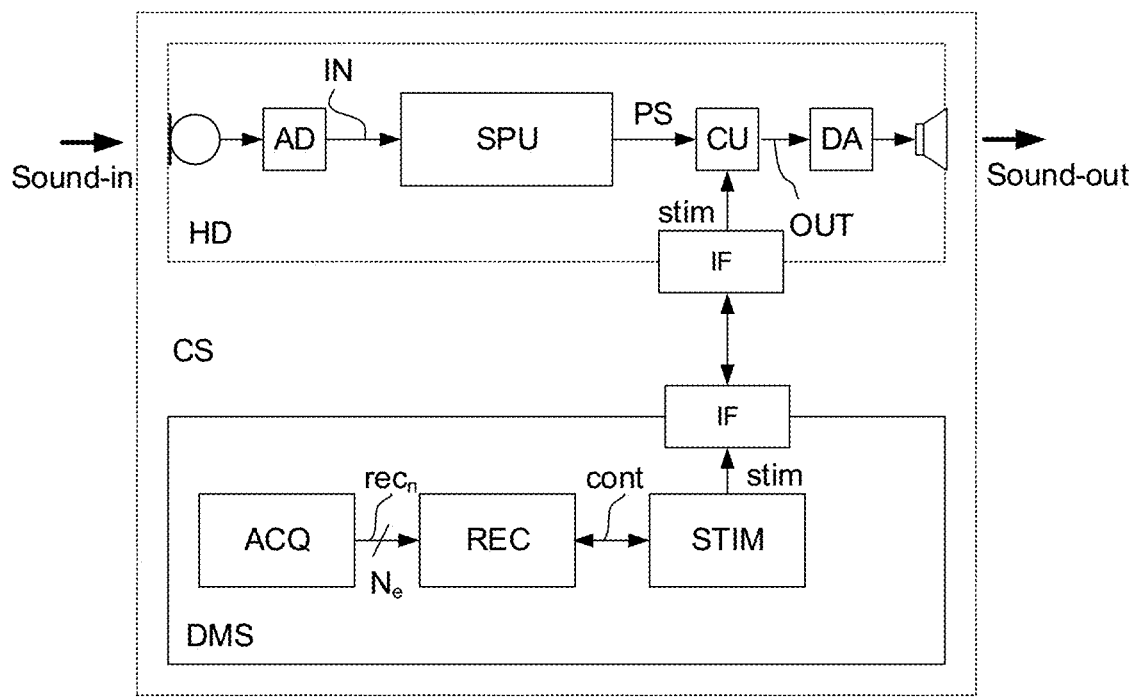
FIG. 8 shows an embodiment of a diagnostic system stimulating a hearing device while worn by a person, wherein stimulation is provided via a loudspeaker of the hearing device.

FIG. 8 shows an embodiment of a combined system (CS) comprising a diagnostic system (DMS) stimulating a hearing device (HD) while worn by a person (U, wherein stimulation stim is transmitted directly to the hearing device (HD) and provided via a loudspeaker (OT) of the hearing device (HD). The embodiment of FIG. 8 is similar to the embodiment of FIG. 5B. The forward path of the hearing device (HD) comprises an input transducer (here a microphone), an analogue to digital converter (AD), signal processing unit (SPU), a combination unit (CO, a digital to analogue converter (DA), and an output transducer (here a loudspeaker). A difference to the embodiment of FIG. 5B is that in the embodiment of FIG. 8, the stimulation signal stim is sent directly from a stimulation unit (STIM) of the diagnostic system (DMS) to a combination unit (CU the hearing device (HD) via an interface (F), (e.g. a wireless interface). The combination unit (CU is configured to allow a stimulation signal stim received from the diagnostic system (DMS) to be presented to a user (U via the loudspeaker (and DA-converter (DA)) of the hearing device (either alone or in combination (mixed with) the processed signal PS from the signal processing unit (SPU) of the forward path of the hearing device (HD). The combination unit may be controlled by the diagnostic system (e.g. by a signal transmitted via the (e.g. wireless) interface (F)).

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

ANSI S3.5. (1997), American National Standard: 'Methods for Calculation of the Speech Intelligibility Index'.

[Cebulla et al., 2007] Cebulla, M., Stürzebecher, E., Elberling, C., and Müller, J. (2007), 'New clicklike stimuli for hearing testing', J. Am. Acad. Audiol., 18, 725-738.

[Chang et al.; 2012] Chang H.-W., Dillon, H., Carter, L., Van Dun, B., and Young, S.-T. (2012), 'The relationship between cortical auditory evoked potential (CAEP) detection and estimated audibility in infants with sensorineural hearing loss', Int. J. Audiol., 51, 663-670.

[Elberling, 2005], Elberling, C. (2005), 'Method to design acoustic stimuli in spectral domain for the recording of auditory steady-state responses (ASSR)', U.S. Pat. No. 8,591,433 B2 (Nov. 26, 2013).

[Elberling et al., 2007a], Elberling, C., Don, M., Cebulla, M., and Stürzebecher, E. (2007), 'Auditory steady-state responses to chirp stimuli based on cochlear traveling wave delay', J. Acoust. Soc. Am., 122(5), 2772-2785.

[Elberling et al., 2007b] Elberling, C., Cebulla, M., & Stürzebecher, E. (2007), 'Simultaneous multiple stimulation of the ASSR'. In: 1st *International Symposium on Auditory and Audiological Research* (*ISAAR* 2007): *Auditory signal processing in hearing-impaired listeners*. Eds. T Dau, J M Buchholz, J M Harte, T U Christensen. Centertryk A/S, Denmark. ISBN 87-990013-1-4. pg. 201-209.

[Elberling & Don, 2010] Elberling, C. and Don, M. (2010), 'A direct approach for the design of chirp stimuli used for the recording of auditory brainstem responses', J. Acoust. Soc. Am., 128(5): 2955-2964.

IEC 60118-15. (2012), Electroacoustics—Hearing aids—Part 15: 'Methods for characterising signal processing in hearing aids with a speech-like signal' (International Electrotechnical Commission, Geneva, Switzerland).

IEC 60318-4. (2010), Electroacoustics-Simulators of Human Head and Ear-Part 4: 'Occluded-Ear Simulator for the Measurement of Earphones Coupled to the Ear by Means of Ear Inserts' (International Electrotechnical Commission, Geneva, Switzerland).

[Kuwada et al.; 2002] Kuwada, S., Anderson, J. S., Batra, R., Fitzpatrick, D. C., Teisser, N. and D'Angelo, W. R. (2002), 'Souraces of the Scalp-Recorded Amplitude Modulation Following Response', J. Am. Acad. Audiol., 13, 188-204.

[Picton et al., 1987] Picton, T. W., Skinner, C. R., Champagne, S. C., Kellett, A. J. C., and Maiste, A. C. (1987), 'Potentials evoked by the sinusoidal modulation of the amplitude or frequency of a tone', J. Acoust. Soc. Am., 82(1), 165-178.

[Plomp; 1984] Plomp, R. (1984), 'Perception of Speech as a Modulated Signal', In Proc. Of the 10$^{th}$ Int. Cong. Of Phon. Sci., Eds. Van der Broecke and Cohen, 29-40.

U.S. Pat. No. 8,591,433 B2 (Maico DIagnostic) 26 Nov. 2013.

WO2006003172A1 (Maico Diagnostic) 12 Jan. 2006

The invention claimed is:

1. A diagnostic system for recording auditory steady-state responses of a person, the system comprising
   a stimulation unit including a frequency generator and an output transducer, the stimulation unit being configured to provide an acoustic stimulus signal, via the output transducer, to an ear of the person, and
   a recording unit including one or more recording electrodes configured to record auditory steady-state responses of the person originating from said acoustic stimulus signal,
   wherein the acoustic stimulus signal is a speech-like stimulus provided as a combination of a series of individual frequency-specific stimuli each corresponding to a low-frequency modulation less than 20 Hz which occurs in speech,
   wherein each individual frequency-specific stimuli includes a specified frequency bandwidth, presentation rate, amplitude and amplitude-modulation, and
   wherein said individual frequency-specific stimuli are different and the presentation rates of said individual frequency-specific stimuli are different and chosen to be appropriate for the recording of the auditory steady-state responses in response to said frequency-specific stimuli and obtaining responses from the appropriate structures of the auditory pathway.

2. A diagnostic system according to claim 1 wherein the stimulation unit is further configured to
   generate, using the frequency generator, a number of different frequency specific stimuli, each including a specific frequency or center frequency and bandwidth, and apply an individual modulation rate or a repetition rate to each of the different frequency specific stimuli;
   spectrally shape the amplitude spectrum of each of the different frequency specific stimuli to provide spectrally shaped frequency specific stimuli to provide that a combined signal corresponds to a long-term spectrum of running speech spoken with a specific vocal effort;
   combine the spectrally shaped frequency specific stimuli to provide a combined broad-band signal; and
   amplitude modulate, using a modulator, either each of the spectrally shaped frequency specific stimuli or the combined broad-band signal with a real or simulated envelope of running speech to provide said speech-like stimulus.

3. A diagnostic system according to claim 1 wherein said specified frequency bandwidth, presentation rate, amplitude and amplitude-modulation of said individual frequency-specific stimuli are predefined.

4. A diagnostic system according to claim 1 wherein the recording unit is configured to record auditory steady-state responses of the person when the person is wearing a hearing device at an ear as well as when the person is not wearing the hearing device at the ear.

5. A combined system comprising a diagnostic system according to claim 1 and a hearing aid for compensating a hearing impairment of a user.

6. A combined system according to claim 5 wherein the output transducer is a loudspeaker.

7. A combined system according to claim 5 wherein the combined system further comprises a wireless link between the diagnostic system and the hearing aid, and
   the hearing aid is configured to receive or generate the different frequency specific stimuli as electric signals d and then present the received or generated electric signals to the user via a loudspeaker of the hearing aid as the acoustic stimulus signal.

8. A combined system according to claim 6 wherein the simulation unit is further configured to play, using the loudspeaker, the different frequency specific stimuli to the hearing aid and
   the hearing aid further comprises a microphone and is configured to pick of the acoustic stimulus signal via the microphone and convert the picked up acoustic signal to an electric input signal that is presented to the user via a loudspeaker of the hearing aid.

9. A combined system according to claim 5 wherein the hearing aid is in a normal mode of operation for processing speech stimuli.

10. A combined system according to claim 5 wherein said acoustic stimulus signal is adapted to include a same input dynamic range as a standardised speech stimulus to thereby excite said hearing aid in a mode of operation similar to speech.

11. A combined system according to claim 10 wherein said acoustic stimulus signal is adapted to include a same input dynamic range as a standardised speech stimulus according to the IEC60118-15 standard.

* * * * *